(12) United States Patent
Geitz et al.

(10) Patent No.: US 9,867,943 B2
(45) Date of Patent: Jan. 16, 2018

(54) APPARATUS AND METHOD FOR TREATING TISSUE

(71) Applicant: Boston Scientific Scimed, Inc., Maple Grove, MI (US)

(72) Inventors: Kurt A. E. Geitz, Sudbury, MA (US); Katie L Krueger, Rochester Hills, MI (US); Joseph A Levendusky, Groton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 218 days.

(21) Appl. No.: 14/190,790

(22) Filed: Feb. 26, 2014

(65) Prior Publication Data

US 2014/0180204 A1 Jun. 26, 2014

Related U.S. Application Data (63) Continuation of application No. 13/588,007, filed on Aug. 17, 2012, now Pat. No. 8,679,112, which is a (Continued)

(51) Int. Cl.
*A61M 35/00* (2006.01)
*A61M 5/20* (2006.01)
(Continued)

(52) U.S. Cl.
CPC ....... *A61M 5/2033* (2013.01); *A61B 17/3468* (2013.01); *A61B 17/3478* (2013.01);
(Continued)

(58) Field of Classification Search
CPC ....... A61B 18/1477; A61B 2018/1425; A61M 5/2033; A61M 2210/106; A61M 5/3158; A61M 5/31585
(Continued)

(56) References Cited

U.S. PATENT DOCUMENTS 3,605,743 A * 9/1971 Arce ............... A61M 5/46
604/157
4,803,075 A 2/1989 Wallace et al.
(Continued)

FOREIGN PATENT DOCUMENTS

CA 2186283 9/1995
WO 9745131 12/1997
(Continued)

OTHER PUBLICATIONS

Walker, R.D. et al., "Injectable Bioglass as a Potential Substitute for Injectable Polytetrafluoroethylene", (Aug. 1992), J. Urol., vol. 148, pp. 645-647.

*Primary Examiner* — Gerald Landry, II (57) ABSTRACT

An apparatus for treating tissue of a mammalian body. In one embodiment, a spring mechanism is carried by first and second tubular members and actuatable for moving a needle from a first position disposed within the distal extremity of the first tubular member to a second position extending distally of the first tubular member. In another embodiment, a nozzle is coupled to the distal extremity of an elongate tubular member for delivering a material into tissue of the mammalian body. In a further embodiment, a flexible elongate member provided with a recess is introduced into a cavity of the body to capture tissue in the recess and electrical energy is applied to such tissue in the recess so as to change the compliance of the tissue.

20 Claims, 6 Drawing Sheets

Related U.S. Application Data continuation of application No. 12/257,061, filed on Oct. 23, 2008, now Pat. No. 8,262,626.

(60) Provisional application No. 61/000,157, filed on Oct. 23, 2007.

(51) Int. Cl.
*A61B 17/34* (2006.01)
*A61B 18/18* (2006.01)
*A61M 5/14* (2006.01)
*A61M 5/30* (2006.01)
*A61B 18/14* (2006.01)
*A61B 10/02* (2006.01)
*A61B 17/00* (2006.01)
*A61B 17/30* (2006.01)
*A61B 18/00* (2006.01)

(52) U.S. Cl.
CPC .......... *A61B 18/1492* (2013.01); *A61B 18/18* (2013.01); *A61M 5/14* (2013.01); *A61M 5/30* (2013.01); *A61B 18/1477* (2013.01); *A61B 2010/0208* (2013.01); *A61B 2017/0034* (2013.01); *A61B 2017/00296* (2013.01); *A61B 2017/00827* (2013.01); *A61B 2017/306* (2013.01); *A61B 2018/00291* (2013.01); *A61B 2018/1425* (2013.01); *A61B 2018/1495* (2013.01)

(58) Field of Classification Search
USPC .................. 604/70, 195, 257; 606/21, 41
See application file for complete search history.

(56) References Cited

U.S. PATENT DOCUMENTS

| | | |
|---|---|---|
| 5,007,940 A | 4/1991 | Berg |
| 5,116,387 A | 5/1992 | Berg |
| 5,158,573 A | 10/1992 | Berg |
| 5,256,152 A | 10/1993 | Marks |
| 5,451,406 A | 9/1995 | Lawin et al. |
| 5,536,267 A | 7/1996 | Edwards et al. |
| 5,580,568 A | 12/1996 | Greff et al. |
| 5,667,767 A | 9/1997 | Greff et al. |
| 5,695,480 A | 12/1997 | Evans et al. |
| 5,855,615 A | 1/1999 | Bley et al. |
| 5,935,113 A | 8/1999 | Dysarz |
| 5,976,111 A | 11/1999 | Hart |
| 6,024,739 A | 2/2000 | Ponzi et al. |
| 6,098,629 A | 8/2000 | Johnson et al. |
| 6,193,717 B1 | 2/2001 | Ouchi |
| 6,238,335 B1 | 5/2001 | Silverman et al. |
| 6,251,063 B1 | 6/2001 | Silverman et al. |
| 6,251,064 B1 | 6/2001 | Silverman et al. |
| 6,254,598 B1* | 7/2001 | Edwards ............ A61B 18/1206 606/41 |
| 6,296,607 B1 | 10/2001 | Milbocker |
| 6,338,345 B1 | 1/2002 | Johnson et al. |
| 6,358,197 B1* | 3/2002 | Silverman ................. A61F 2/04 600/29 |
| 6,475,213 B1 | 11/2002 | Whayne et al. |
| 6,524,327 B1 | 2/2003 | Spacek |
| 6,575,896 B2 | 6/2003 | Silverman et al. |
| 6,695,764 B2 | 2/2004 | Silverman et al. |
| 6,749,617 B1* | 6/2004 | Palasis ............... A61B 17/3468 606/167 |
| 6,991,633 B2 | 1/2006 | Agbodoe |
| 7,238,182 B2 | 7/2007 | Swoyer et al. |
| 7,282,050 B2 | 10/2007 | Starkebaum et al. |
| 7,543,589 B2 | 6/2009 | Hooven |
| 2002/0004650 A1 | 1/2002 | Kuracina et al. |
| 2002/0049363 A1 | 4/2002 | Milbocker |
| 2002/0143289 A1* | 10/2002 | Ellis .................... A61B 17/3468 604/22 |
| 2002/0177847 A1 | 11/2002 | Long |
| 2003/0135238 A1 | 7/2003 | Milbocker |
| 2003/0199731 A1* | 10/2003 | Silverman ........ A61B 17/12031 600/29 |
| 2004/0034371 A1* | 2/2004 | Lehman ............. A61B 18/1485 606/144 |
| 2004/0243211 A1* | 12/2004 | Colliou .............. A61N 1/36007 607/133 |
| 2005/0096629 A1 | 5/2005 | Gerber et al. |
| 2005/0096638 A1* | 5/2005 | Starkebaum ........ A61B 5/04884 606/2 |
| 2005/0182342 A1* | 8/2005 | Dinsmoor .............. A61B 5/073 600/593 |
| 2005/0209653 A1* | 9/2005 | Herbert ................ A61N 1/0517 607/40 |
| 2005/0222537 A1 | 10/2005 | Dinsmoor et al. |
| 2005/0245788 A1* | 11/2005 | Gerber ............... A61B 1/00082 600/115 |
| 2006/0100614 A1* | 5/2006 | Long ...................... A61B 18/14 606/27 |
| 2006/0189940 A1* | 8/2006 | Kirsch ............... A61B 17/3478 604/164.1 |
| 2007/0129735 A1* | 6/2007 | Filipi .................. A61B 17/0469 606/144 |
| 2007/0179535 A1* | 8/2007 | Morrissey ............. C12M 35/02 607/3 |
| 2007/0219566 A1 | 9/2007 | Gambale |
| 2008/0058798 A1 | 3/2008 | Wallace et al. |
| 2009/0018602 A1* | 1/2009 | Mitelberg ...... A61B 17/320783 607/40 |
| 2009/0062788 A1* | 3/2009 | Long ..................... A61B 18/14 606/41 |

FOREIGN PATENT DOCUMENTS

| | | |
|---|---|---|
| WO | 0033908 | 6/2000 |
| WO | 0170114 | 9/2001 |

* cited by examiner

APPARATUS AND METHOD FOR TREATING TISSUE

CROSS-REFERENCE TO RELATED APPLICATIONS

This application is a continuation of U.S. patent application Ser. No. 13/588,007 filed Aug. 17, 2012, entitled "Apparatus and Method for Treating Tissue," which is a continuation of U.S. patent application Ser. No. 12/257,061, filed Oct. 23, 2008, now U.S. Pat. No. 8,262,626, entitled "Apparatus and Method for Treating Tissue," which claims the benefit of U.S. patent application Ser. No. 61/000,157, filed Oct. 23, 2007, entitled "Apparatus and Method for Treating Tissue", each of which U.S. patent applications is hereby incorporated by reference in its entirety.

SCOPE OF THE INVENTION

The present invention relates to apparatus and methods for treating a mammalian body and more particularly to apparatus and methods for treating tissue in a wall of a mammalian body.

BACKGROUND

Medical devices have been provided for the delivery of material to various portions of the wall forming a vessel of a mammalian body, such as the gastrointestinal tract, to create implants in the wall. See, for example, U.S. Pat. No. 6,251,063. In addition, apparatus for bulking the wall of the esophagus have been provided. See, for example, U.S. Pat. Nos. 6,098,629 and 6,338,345. Apparatus have also been provided for enhancing the repeatability of implant forming procedures. See, for example, U.S. Pat. No. 6,358,197. Radio frequency treatment devices have also been provided. See, for example, U.S. Pat. No. 6,254,598. There remains, however, a need for injection devices that facilitate repeatable injections, as well as other device for treating the tissue in the wall of a mammalian body.

SUMMARY OF THE INVENTION

An apparatus for treating tissue of a mammalian body is provided. In one embodiment, a spring mechanism is carried by first and second tubular members and actuatable for moving a needle from a first position disposed within the distal extremity of the first tubular member to a second position extending distally of the first tubular member. In another embodiment, a nozzle is coupled to the distal extremity of an elongate tubular member for delivering a material into tissue of the mammalian body. In a further embodiment, a flexible elongate member provided with a recess is introducing into a cavity of the body to capture tissue in the recess and electrical energy is applied to such tissue in the recess so as to change the compliance of the tissue.

BRIEF DESCRIPTION OF THE DRAWINGS

The accompanying drawings, which are somewhat schematic in some instances and are incorporated in and form a part of this specification, illustrate several embodiments of the invention and, together with the description, serve to explain the principles of the invention.

DESCRIPTION OF THE INVENTION

The method of the present invention for treating tissue can be performed with an suitable apparatus or medical device such as of the type shown in FIGS. 1-5. Medical device 21 of FIG. 1 includes a probe member or probe 22 having an optical viewing device 23. A tissue capture member or tissue acquisition cap 26 is coupled to the distal end portion of probe 22 and an injection device or apparatus 27 is slidably carried by probe 22. Treatment device 21 further includes a supply 28 of a suitable injectable material coupled to the injection apparatus 27.

A conventional or other suitable gastroscope or endoscope can be used for probe or catheter 22. Exemplary probe 22 includes a flexible elongate tubular member or insertion tube 31 having a proximal extremity or portion 31a, a distal extremity or portion 31b and a distal face 32. Insertion tube 31 has been sectioned in FIG. 1 so that only a portion of proximal extremity 31a and distal extremity 31b are shown. A handle means or assembly is coupled to proximal extremity 31a of the insertion tube 31 and includes a conventional handle 33. The tubular insertion tube 31 is provided with at least one bore and preferably a plurality of bores or passageways 36 extending from proximal extremity 31a to distal extremity 31b. A portion of one such passageway 36, having an internal diameter which can approximate 2.8 millimeters, is shown in dashed lines in FIG. 3.

Figures 1, 2, 3:
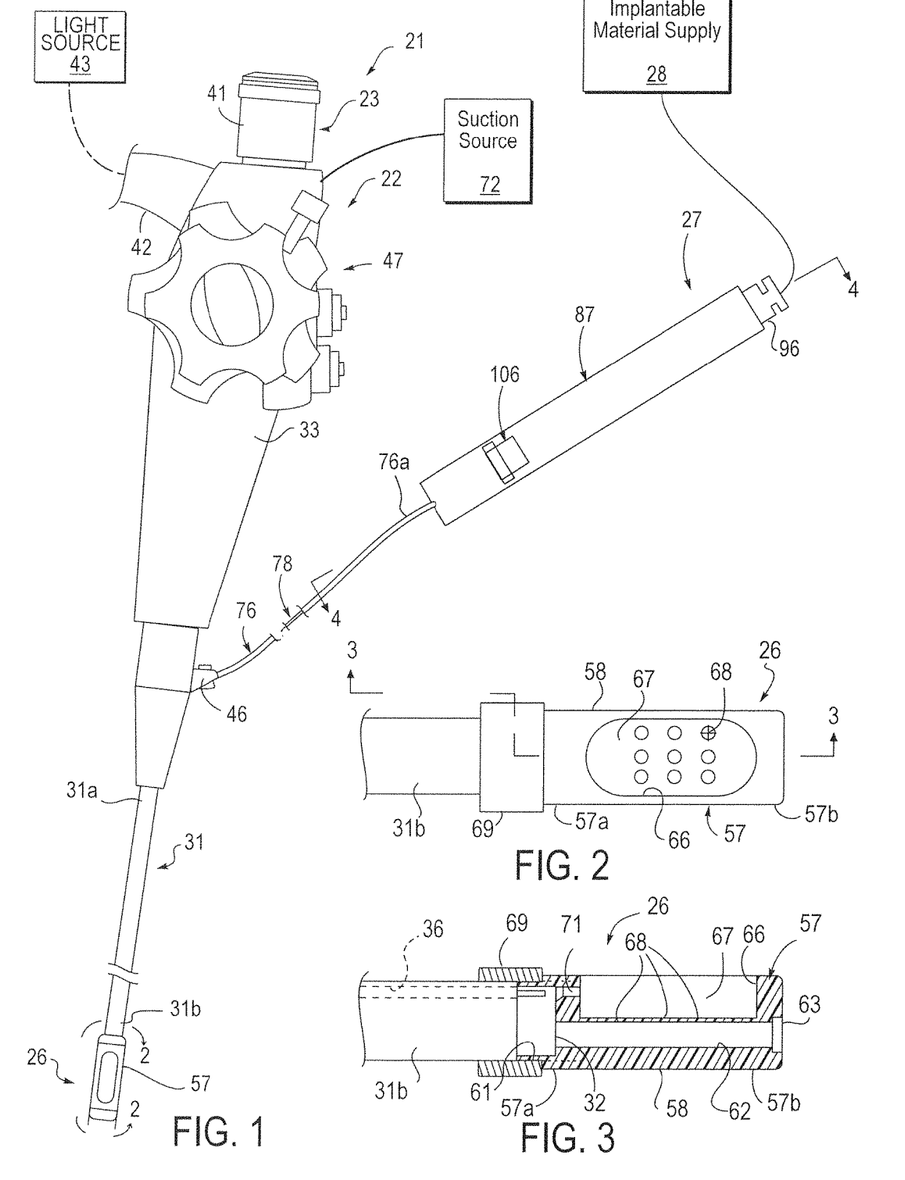
FIG. 1 is a plan view of an apparatus for treating tissue in accordance with one embodiment of the present invention.
FIG. 2 is an enlarged view of the distal extremity of the apparatus for treating tissue of FIG. 1 taken along the line 2-2 of FIG. 1.
FIG. 3 is a cross-sectional view of the distal extremity of the apparatus for treating tissue of FIG. 1 taken along the line 3-3 of FIG. 2.

Optical viewing device 23 is formed integral with probe 22 and has an optical element or objective lens (not shown) carried by one of the passageways 36 of the probe 22. The optical viewing device can include a fiber optic or other optical element that extends through probe 22 to the lens, or can include an optical sensor or camera at the distal end of the probe, such as a CCD or CMOS sensor, for serving as the objective lens. The objective lens has a field of view at distal face 32 which permits the operator to view forwardly of insertion tube distal extremity 31b. Optical viewing device 23 further includes an eye piece 41 mounted on the proximal end of handle 33. A connection cable 42, a portion of which is shown in FIG. 1, extends from handle 33 to a conventional light source 43. At least one light guide (not shown) extends through cable 42 and insertion tube 31 for providing illumination forwardly of distal face 32 of the insertion tube 31.

One of the passageways 36 provided in insertion tube 31 extends to a side port 46 formed in handle 33. Injection apparatus 27 can be slidably introduced into such passageway 36 by means of side port 46. Insertion tube 31 is flexible so as to facilitate its insertion and advancement through a body and is provided with a bendable distal end for selectively directing distal face 32 in a desired direction. A plurality of finger operable controls 47 are provided on handle 33 for, among other things, operating the bendable distal end of insertion tube 31 and the supply and removal of fluids through the insertion tube 31.

An overtip assembly or tissue capture member 26 is preferably carried by distal extremity 31b of the insertion tube 31 (see FIGS. 1-3). Although any suitable member can be provided for capturing tissue for treatment, tissue capture member 26 includes a body or end cap 57, which is preferably cylindrical in conformation, made from any suitable material such as plastic. An optically clear plastic is preferred to permit visualization through the end cap 57. The end cap 57 has a diameter ranging from 0.5 to 2.5 centimeters and preferably ranging from 0.75 to 1.5 centimeters and a length ranging from two to eight centimeters and preferably ranging from three to five centimeters. The end cap has a proximal end 57a and a distal end 57b and an outer surface 58 extending between the ends 57a and 57b. A longitudinally-extending cavity 61 is provided at the proximal end 57a of the end cap and a central bore 62 extends distally from cavity 61 to the distal end 57b of the end cap 57. An optional optical window 63 is provided at the distal end of bore 62 and is sealably secured to distal end 57b so as to seal the distal opening of bore 62.

At least one and as shown one vacuum recess or cavity 66 is provided in outer cylindrical surface 58 of end cap 57. The recess or suction chamber 66 is of any suitable size and shape, preferably having a length ranging from 0.5 to five centimeters, more preferably approximately two centimeters, and extending circumferentially over an angle ranging from 30 to 180 degrees, more preferably approximately 90 degrees. The chamber 66 is preferably formed in part by a planar wall or base 67. A plurality of bores or apertures 68 extend through base 67 to fluidly connect the suction chamber 66 with central bore 62.

A outer sheath or other suitable connector 69 is included in tissue capture member 26 for removably mounting end cap 57 to distal extremity 31b of the insertion tube 31. The outer sheath 69 is made from any suitable material such as silicon and is fixed in any suitable manner to proximal end 57a of the end cap. The outer sheath is diametrically sized and has sufficient elasticity to extend over a portion of distal extremity 31b and secure thereto, for example with a friction fit. The proximal end 57a of the end cap 57 generally abuts distal extremity 31b when tissue capture member 26 is so secured to insertion tube 31. Outer sheath 69 further serves as a seal to provide a fluid-tight connection between the end cap 57 and the insertion tube 31. At least one longitudinally-extending bore or guide 71 extends from the distal end of cavity 61 to the proximal end of suction chamber 66 for providing access from a tool carried by probe 22 to the suction chamber.

A suction source 72 can be included with medical device 21 for use with probe 22 and tissue capture member 26. The suction source 72, shown schematically in FIG. 1, is coupled to the probe 22 for fluid communication with one of the passageways of insertion tube 31 and thus central bore 62 and suction chamber 66 of the tissue capture member 26.

Figure 4:
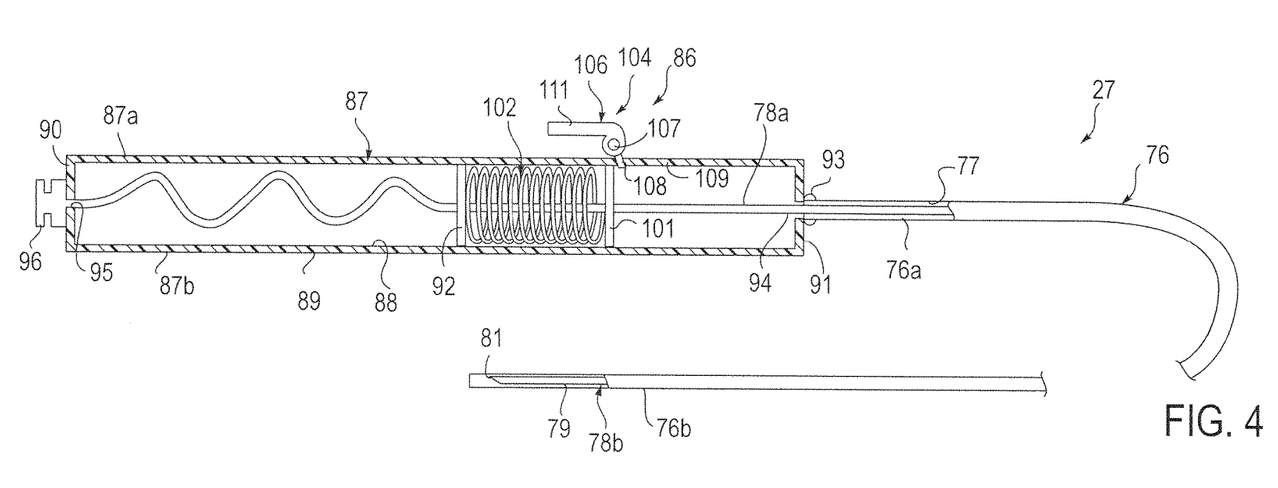
FIG. 4 is a side view, partially cross sectioned along the line 4-4 of FIG. 1 and partially cut away at its distal extremity, of an injection device included as part of the apparatus for treating tissue of FIG. 1.
Figure 5:
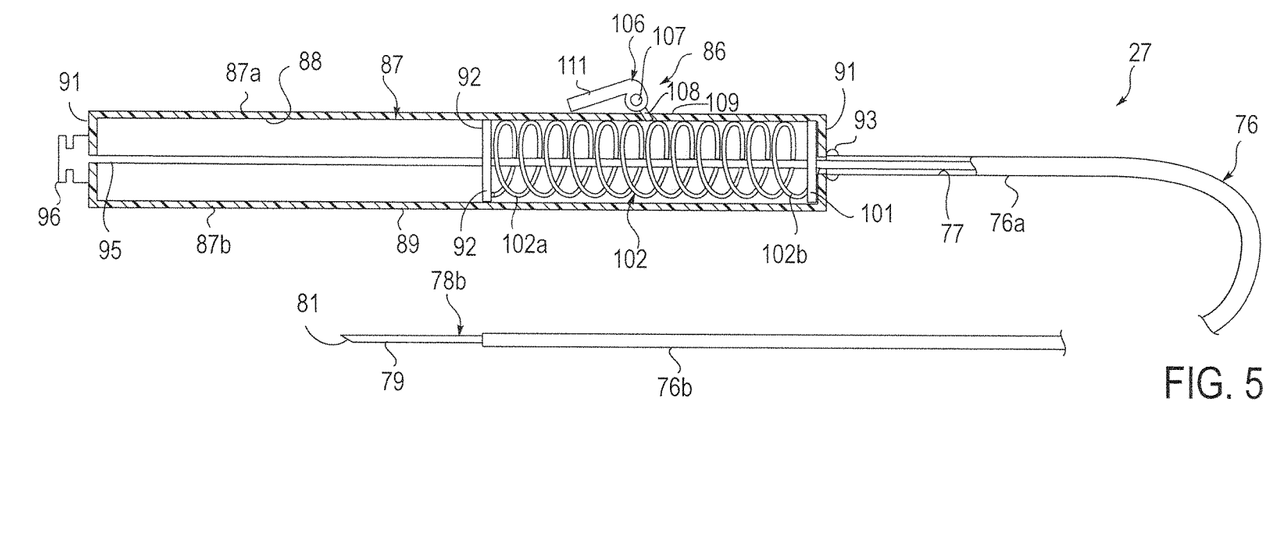
FIG. 5 is a side view, similar to FIG. 4, of the injection device of FIG. 4 in a second position.

Injection apparatus 27 includes a first tubular member or outer sheath 76, made from any suitable material such as plastic, that is preferably flexible (see FIGS. 1, 4 and 5). The outer sheath or outer sheath 76 has a proximal extremity 76a and a distal extremity 76b and is provided with a lumen 77 extending from the proximal extremity 76a to the distal extremity 76b. Outer sheath 76 is diametrically sized for slidable disposition within passageway 36 of probe 22 and, more specifically, has an outer diameter ranging from 1.5 to 3.0 millimeters and preferably approximately 2.3 millimeters. A second tubular member or inner sheath 78 is slidably disposed within lumen 77 of outer sheath 76. The needle member or inner sheath 78 has a proximal end portion 78a and a distal end portion 78b. Although the inner sheath 78 can be a unitary structure, for example made from plastic or any other suitable material, in one preferred embodiment the proximal and central portions of the inner sheath are made from plastic and the distal end portion 78b includes a needle 79 secured to such plastic material by any suitable means. The needle 79 includes a tissue penetrating tip 81. An internal passageway (not shown) extends from proximal end portion 78a of the inner sheath to an opening (not shown) provided in needle 79 and preferably provided at the distal tip 81 of the needle. Inner sheath 78 is slidably moveable within lumen 77 of outer sheath 76 between a first position in which needle 79 is disposed within distal extremity 76b of the outer sheath, as shown in FIG. 4, and a second position in which the needle 79 extends distally from the distal extremity 76b of the outer sheath, as shown in FIG. 5.

A spring mechanism 86 is carried by proximal extremities of outer sheath 76 and inner sheath 78 for moving the inner sheath from its first position to its second position. It is appreciated that the spring mechanism can be of several configurations and designs. One embodiment of the spring mechanism 86 is shown in FIGS. 4-5 and includes a hand-grippable member in the form of an elongate tubular housing 87 made from a suitable material such as plastic. The housing 87 is formed, for example, by first and second shells 87a and 87b, and is provided with a longitudinally-extending internal chamber 88 formed by an outer cylindrical wall 89 joined to a proximal end wall 90 and an opposite distal end wall 91. An internal wall or counter plate 92 made from plastic or any suitable material extends transversely across internal chamber 88 and is secured at its periphery by any suitable means to the inside of cylindrical wall 89.

Proximal extremity 76a of the outer sheath is secured to distal end wall 91 by any suitable means such as an adhesive 93. An opening 94 is provided in the distal end wall for permitting communication between lumen 77 of the outer sheath 76 and internal chamber 92 of the housing 87. Proximal end portion 78a of the inner sheath 78 slidably enters chamber 88 through opening 94 and slidably passes through an opening (not shown) in counter plate 92. A proximal end of the inner sheath 78 passes through an opening 95 provided in proximal end wall 90 so as to communicate with a conventional fitting or connector, such as a luer fitting 96, mounted on the outside of proximal end wall 90.

Spring mechanism 86 includes a slide member or slide 101 disposed within internal chamber 88 between counter plate 92 and distal end wall 91 for longitudinal movement within the chamber 88. The slide 101 can be of any suitable type, such as a disc or cylinder, and preferably has an outer periphery having a size and configuration approximating the internal surface of cylindrical wall 89 so as to facilitate slidable movement of the slide 101 within chamber 88. The slide 101 is provided with an opening or hole (not shown) through which the proximal end portion 78a of the inner sheath 78 extends and the slide 101 is rigidly mounted about inner sheath 78 for one-to-one longitudinal movement with the inner sheath. A spring member of any suitable type, for example a coil spring 102, is concentrically disposed about inner sheath 78 and has a proximal end 102a seated against counter plate 92 and a distal end 102b seated against slide 101. Slide 101 is movable by coil spring 102 between a first position, shown in FIG. 4 in which the spring 102 is in a compressed position, and a second position, shown in FIG. 5, in which slide 101 is being urged by the spring 102 against distal end wall 91 of the housing 87. A sufficient portion of flexible inner sheath 78 is disposed within internal chamber 88 so as to permit the movement of slide 101 from its first position to its second position. In this regard, the compression of the proximal end of inner sheath 78 when slide 101 is in its first position causes such proximal end of the inner sheath to bunch or buckle within the portion of chamber 88 between proximal end wall 90 and counter plate 92.

Spring mechanism 86 includes a locking mechanisms 104 for retaining slide 101 in its first position against the force of compressed coil spring 102. The locking mechanism 104 is of any suitable type and in one embodiment includes a finger-operable element 106 pivotably coupled to housing 87 by means of a pin 107 and moveable between a first or locked position, shown in FIG. 4, and a second or unlocked position, shown in FIG. 5. Finger-operable or locking member 106 includes a latch 108 which extends through an opening, such as a slot 109, provided in cylindrical wall 89 for engaging slide 101 in its first position. The locking element 106 further includes a lever of trigger 111 which can be actuated by a finger, such as the thumb, for pivoting latch 108 about pin 107 from its first position of FIG. 4 to its second position of FIG. 5.

When slide 101 is in its first position, needle 79 is in its first position recessed within distal extremity 76b of the outer sheath 76, as shown in FIG. 4. When slide 101 is in its second position, the needle is in its second position in which the needle extends distally from sheath distal extremity 76b, as shown FIG. 5. Needle 79 has a travel between its first and second positions ranging from four to 25 millimeters and preferably ranging from 10 to 20 millimeters. As can be appreciated, the travel distance of needle 79 is determined by the distance between slide 101, in its first position shown in FIG. 4, and distal end wall 91.

Any suitable mechanism can be included in injection apparatus 27 for returning slide 101 to its first or locked position, shown in FIG. 4. For example, one or more tabs (not shown) can extend radially from the slide and through respective slots (not shown) provided in housing 87. The one or more slots in the housing 87 would preferably have a length at least equal to the distance slide 101 travels between its first and second positions. The one or more radially-extending tabs are configured to be engaged by a human hand for urging the slide 101 rearwardly, under the force of coil spring 102, from its second position to its first position.

A supply or reservoir 28 or any suitable type is coupled to the proximal extremity of injection apparatus 27, and preferably to the proximal end portion 78a of inner sheath 78. For example, one or more syringes for containing an implantable or other injectable material, or the ingredients thereof, can be included in supply 28. It is appreciated that the injectable material for use in the methods and apparatus of the present invention can include any suitable material such as a treatment agent, antibiotic or analgesic. Supply 28 is included within the means of medical or treatment device 21 for introducing at least one liquid, solution, composition or material through lumen 77 of inner sheath 78 and out at least one opening at the distal end portion 78b of the inner sheath.

Exemplary implantable materials or compositions which can be included in supply 28 and thus utilized in accordance with one embodiment of the method and apparatus of the present invention include any suitable material or composition from which an implant can be formed when a fluid, separately or in conjunction with another fluid, is introduced into the tissue of a body. The implant-forming material hereof includes solutions. Although aqueous or nonaqueous solutions are among the fluids that can be used, an inert, nonresorbable material is preferred. Preferred nonaqueous solutions are any of the solutions disclosed in International Application No. PCT/US99/29427 filed Dec. 10, 1999, the entire content of which is incorporated herein by this reference. One such injectable or implant-forming material comprises at least one solution which when introduced into the body forms a nonbiodegradable solid. As used herein, a solid means any substance that does not flow perceptibly under moderate stress, has a definite capacity for resisting forces which tend to deform it (such as compression, tension and strain) and under ordinary conditions retains a definite size and shape; such a solid includes, without limitation, spongy and/or porous substances. One such embodiment of the at least one solution is first and second solutions which when combined in the body form the nonbiodegradable solid. Another such embodiment is a solution which can be introduced into the body as a liquid and from which a solid thereafter precipitates or otherwise forms. A preferred embodiment of such a solution is a solution of a biocompatible composition and an optional biocompatible solvent which can further optionally include a contrast agent for facilitating visualization of the solution in the body. The solution can be aqueous or nonaqueous. Exemplary biocompatible compositions include biocompatible prepolymers and biocompatible polymers.

A particularly preferred implant forming solution is a composition comprising from about 2.5 to about 8.0 weight percent of a biocompatible polymer, from about 52 to about 87.5 weight percent of a biocompatible solvent and optionally from about 10 to about 40 weight percent of a biocompatible contrast agent having a preferred average particle size of about 10 µm or less. It should be appreciated that any percents stated herein which include a contrast agent would be proportionally adjusted when the contrast agent is not utilized. Any contrast agent is preferably a water insoluble biocompatible contrast agent. The weight percent of the polymer, contrast agent and biocompatible solvent is based on the total weight of the complete composition. In a preferred embodiment, the water insoluble, biocompatible contrast agent is selected from the group consisting of barium sulfate, tantalum powder and tantalum oxide. In still a further preferred embodiment, the biocompatible solvent is dimethylsulfoxide (DMSO), ethanol, ethyl lactate or acetone.

The term "biocompatible polymer" refers to polymers which, in the amounts employed, are non-toxic, chemically inert, and substantially non-immunogenic when used internally in the patient and which are substantially insoluble in physiologic liquids. Suitable biocompatible polymers include, by way of example, cellulose acetates (including cellulose diacetate), ethylene vinyl alcohol copolymers, hydrogels (e.g., acrylics), poly(C1-C6) acrylates, acrylate copolymers, polyalkyl alkacrylates wherein the alkyl and alk groups independently contain one to six carbon atoms, polyacrylonitrile, polyvinylacetate, cellulose acetate butyrate, nitrocellulose, copolymers of urethane/carbonate, copolymers of styrene/maleic acid, and mixtures thereof. Copolymers of urethane/carbonate include polycarbonates that are diol terminated which are then reacted with a diisocyanate such as methylene bisphenyl diisocyanate to provide for the urethane/carbonate copolymers. Likewise, copolymers of styrene/maleic acid refer to copolymers having a ratio of styrene to maleic acid of from about 7:3 to about 3:7. Preferably, the biocompatible polymer is also non-inflammatory when employed in situ. The particular biocompatible polymer employed is not critical and is selected relative to the viscosity of the resulting polymer solution, the solubility of the biocompatible polymer in the biocompatible solvent, and the like. Such factors are well within the skill of the art.

The polymers of polyacrylonitrile, polyvinylacetate, poly (C1-C6) acrylates, acrylate copolymers, polyalkyl alkacrylates wherein the alkyl and alk groups independently contain one to six carbon atoms, cellulose acetate butyrate, nitrocellulose, copolymers of urethane/carbonate, copolymers of styrene/maleic acid and mixtures thereof typically will have a molecular weight of at least about 50,000 and more preferably from about 75,000 to about 300,000.

Preferred biocompatible polymers include cellulose diacetate and ethylene vinyl alcohol copolymer. In one embodiment, the cellulose diacetate has an acetyl content of from about 31 to about 40 weight percent. Cellulose diacetate polymers are either commercially available or can be prepared by art recognized procedures. In a preferred embodiment, the number average molecular weight, as determined by gel permeation chromatography, of the cellulose diacetate composition is from about 25,000 to about 100,000 more preferably from about 50,000 to about 75,000 and still more preferably from about 58,000 to about 64,000. The weight average molecular weight of the cellulose diacetate composition, as determined by gel permeation chromatography, is preferably from about 50,000 to 200,000 and more preferably from about 100,000 to about 180,000. As is apparent to one skilled in the art, with all other factors being equal, cellulose diacetate polymers having a lower molecular weight will impart a lower viscosity to the composition as compared to higher molecular weight polymers. Accordingly, adjustment of the viscosity of the composition can be readily achieved by mere adjustment of the molecular weight of the polymer composition.

Ethylene vinyl alcohol copolymers comprise residues of both ethylene and vinyl alcohol monomers. Small amounts (e.g., less than 5 mole percent) of additional monomers can be included in the polymer structure or grafted thereon provided such additional monomers do not alter the implanting properties of the composition. Such additional monomers include, by way of example only, maleic anhydride, styrene, propylene, acrylic acid, vinyl acetate and the like.

Ethylene vinyl alcohol copolymers are either commercially available or can be prepared by art recognized procedures. Preferably, the ethylene vinyl alcohol copolymer composition is selected such that a solution of 8 weight-volume percent of the ethylene vinyl alcohol copolymer in DMSO has a viscosity equal to or less than 60 centipoise at 20° C. and more preferably 40 centipoise or less at 20° C. As is apparent to one skilled in the art, with all other factors being equal, copolymers having a lower molecular weight will impart a lower viscosity to the composition as compared to higher molecular weight copolymers. Accordingly, adjustment of the viscosity of the composition as necessary for catheter delivery can be readily achieved by mere adjustment of the molecular weight of the copolymer composition.

As is also apparent, the ratio of ethylene to vinyl alcohol in the copolymer affects the overall hydrophobicity/hydrophilicity of the composition which, in turn, affects the relative water solubility/insolubility of the composition as well as the rate of precipitation of the copolymer in an aqueous solution. In a particularly preferred embodiment, the copolymers employed herein comprise a mole percent of ethylene of from about 25 to about 60 and a mole percent of vinyl alcohol of from about 40 to about 75, more preferably a mole percent of ethylene of from about 40 to about 60 and a mole percent of vinyl alcohol of from about 40 to about 60.

The term "contrast agent" refers to a biocompatible (non-toxic) radiopaque material capable of being monitored during injection into a mammalian subject by, for example, radiography. The contrast agent can be either water soluble or water insoluble. Examples of water soluble contrast agents include metrizamide, iopamidol, iothalamate sodium, iodomide sodium, and meglumine. The term "water insoluble contrast agent" refers to contrast agents which are insoluble in water (i.e., has a water solubility of less than 0.01 milligrams per milliliter at 20° C.) and include tantalum, tantalum oxide and barium sulfate, each of which is commercially available in the proper form for in vivo use and preferably having a particle size of 10 μm or less. Other water insoluble contrast agents include gold, tungsten and platinum powders. Methods for preparing such water insoluble biocompatible contrast agents having an average particle size of about 10 μm or less are described below. Preferably, the contrast agent is water insoluble (i.e., has a water solubility of less than 0.01 mg/ml at 20° C.)

The term "encapsulation" as used relative to the contrast agent being encapsulated in the precipitate is not meant to infer any physical entrapment of the contrast agent within the precipitate much as a capsule encapsulates a medicament. Rather, this term is used to mean that an integral coherent precipitate forms which does not separate into individual components, for example into a copolymer component and a contrast agent component.

The term "biocompatible solvent" refers to an organic material liquid at least at body temperature of the mammal in which the biocompatible polymer is soluble and, in the amounts used, is substantially non-toxic. Suitable biocompatible solvents include, by way of example, dimethylsulfoxide, analogues/homologues of dimethylsulfoxide, ethanol, ethyl lactate, acetone, and the like. Aqueous mixtures with the biocompatible solvent can also be employed provided that the amount of water employed is sufficiently small that the dissolved polymer precipitates upon injection into a human body. Preferably, the biocompatible solvent is ethyl lactate or dimethylsulfoxide.

The compositions employed in the methods of this invention are prepared by conventional methods whereby each of the components is added and the resulting composition mixed together until the overall composition is substantially homogeneous. For example, sufficient amounts of the selected polymer are added to the biocompatible solvent to achieve the effective concentration for the complete composition. Preferably, the composition will comprise from about 2.5 to about 8.0 weight percent of the polymer based on the total weight of the composition and more preferably from about 4 to about 5.2 weight percent. If necessary, gentle heating and stirring can be used to effect dissolution of the polymer into the biocompatible solvent, e.g., 12 hours at 50° C.

Sufficient amounts of the contrast agent are then optionally added to the biocompatible solvent to achieve the effective concentration for the complete composition. Preferably, the composition will comprise from about 10 to about 40 weight percent of the contrast agent and more preferably from about 20 to about 40 weight percent and even more preferably about 30 to about 35 weight percent. When the contrast agent is not soluble in the biocompatible solvent, stirring is employed to effect homogeneity of the resulting suspension. In order to enhance formation of the suspension, the particle size of the contrast agent is preferably maintained at about 10 µm or less and more preferably at from about 1 to about 5 µm (e.g., an average size of about 2 µm). In one preferred embodiment, the appropriate particle size of the contrast agent is prepared, for example, by fractionation. In such an embodiment, a water insoluble contrast agent such as tantalum having an average particle size of less than about 20 microns is added to an organic liquid such as ethanol (absolute) preferably in a clean environment. Agitation of the resulting suspension followed by settling for approximately 40 seconds permits the larger particles to settle faster. Removal of the upper portion of the organic liquid followed by separation of the liquid from the particles results in a reduction of the particle size which is confirmed under an optical microscope. The process is optionally repeated until a desired average particle size is reached.

The particular order of addition of components to the biocompatible solvent is not critical and stirring of the resulting suspension is conducted as necessary to achieve homogeneity of the composition. Preferably, mixing/stirring of the composition is conducted under an anhydrous atmosphere at ambient pressure. The resulting composition is heat sterilized and then stored preferably in sealed amber bottles or vials until needed.

Each of the polymers recited herein is commercially available but can also be prepared by methods well known in the art. For example, polymers are typically prepared by conventional techniques such as radical, thermal, UV, gamma irradiation, or electron beam induced polymerization employing, as necessary, a polymerization catalyst or polymerization initiator to provide for the polymer composition. The specific manner of polymerization is not critical and the polymerization techniques employed do not form a part of this invention. In order to maintain solubility in the biocompatible solvent, the polymers described herein are preferably not cross-linked.

In another particularly preferred embodiment of the nonaqueous solution, the biocompatible polymer composition can be replaced with a biocompatible prepolymer composition containing a biocompatible prepolymer. In this embodiment, the composition comprises a biocompatible prepolymer, an optional biocompatible water insoluble contrast agent preferably having an average particle size of about 10 µm or less and, optionally, a biocompatible solvent.

The term "biocompatible prepolymer" refers to materials which polymerize in situ to form a polymer and which, in the amounts employed, are non-toxic, chemically inert, and substantially non-immunogenic when used internally in the patient and which are substantially insoluble in physiologic liquids. Such a composition is introduced into the body as a mixture of reactive chemicals and thereafter forms a biocompatible polymer within the body. Suitable biocompatible prepolymers include, by way of example, cyanoacrylates, hydroxyethyl methacrylate, silicon prepolymers, and the like. The prepolymer can either be a monomer or a reactive oligomer. Preferably, the biocompatible prepolymer is also non-inflammatory when employed in situ.

Prepolymer compositions can be prepared by adding sufficient amounts of the optional contrast agent to the solution (e.g., liquid prepolymer) to achieve the effective concentration for the complete polymer composition. Preferably, the prepolymer composition will comprise from about 10 to about 40 weight percent of the contrast agent and more preferably from about 20 to about 40 weight percent and even more preferably about 30 weight percent. When the contrast agent is not soluble in the biocompatible prepolymer composition, stirring is employed to effect homogeneity of the resulting suspension. In order to enhance formation of the suspension, the particle size of the contrast agent is preferably maintained at about 10 µm or less and more preferably at from about 1 to about 5 µm (e.g., an average size of about 2 µm).

When the prepolymer is liquid (as in the case of polyurethanes), the use of a biocompatible solvent is not absolutely necessary but may be preferred to provide for an appropriate viscosity in the nonaqueous solution. Preferably, when employed, the biocompatible solvent will comprise from about 10 to about 50 weight percent of the biocompatible prepolymer composition based on the total weight of the prepolymer composition. When a biocompatible solvent is employed, the prepolymeric composition typically comprises from about 90 to about 50 weight percent of the prepolymer based on the total weight of the composition.

In a particularly preferred embodiment, the prepolymer is cyanoacrylate which is preferably employed in the absence of a biocompatible solvent. When so employed, the cyanoacrylate adhesive is selected to have a viscosity of from about 5 to about 20 centipoise at 20° C.

The particular order of addition of components is not critical and stirring of the resulting suspension is conducted as necessary to achieve homogeneity of the composition. Preferably, mixing/stirring of the composition is conducted under an anhydrous atmosphere at ambient pressure. The resulting composition is sterilized and then stored preferably in sealed amber bottles or vials until needed.

Specific embodiments of nonaqueous solutions suitable for use in the apparatus and methods of the invention are described in U.S. Pat. No. 5,667,767 dated Sep. 16, 1997, U.S. Pat. No. 5,580,568 dated Dec. 3, 1996 and U.S. Pat. No. 5,695,480 dated Dec. 9, 1997 and International Publication Number WO 97/45131 having an International Publication Date of Dec. 4, 1997, the entire contents of each of which are incorporated herein by this reference.

Other suitable materials for use with the methods and apparatus of the present invention include any material capable of being delivered through a needle, solutions, suspensions, slurries, biodegradable or nonbiodegradable materials and two part or other mixtures. Exemplary materials include injectable bioglass as described in Walker et al., "Injectable Bioglass as a Potential Substitute for Injectable Polytetrafluorethylene Particles", J. Urol., 148:645-7, 1992, small particle species such as polytetrafluoroethylene (PTFE) particles in glycerine such as Polytef®, biocompatible compositions comprising discrete, polymeric and silicone rubber bodies such as described in U.S. Pat. Nos. 5,007,940, 5,158,573 and 5,116,387 to Berg, biocompatible compositions comprising carbon coated beads such as disclosed in U.S. Pat. No. 5,451,406 to Lawin, collagen and other biodegradable material of the type disclosed in U.S. Pat. No. 4,803,075 to Wallace et al., biocompatible materials such as disclosed in U.S. Pat. No. 6,296,607 to Milbocker, U.S. Pat. No. 6,524,327 to Spacek, and U.S. Publication Nos. 2002/0049363 and 2003/0135238 to Milbocker, and other known injectable materials.

Figure 6:
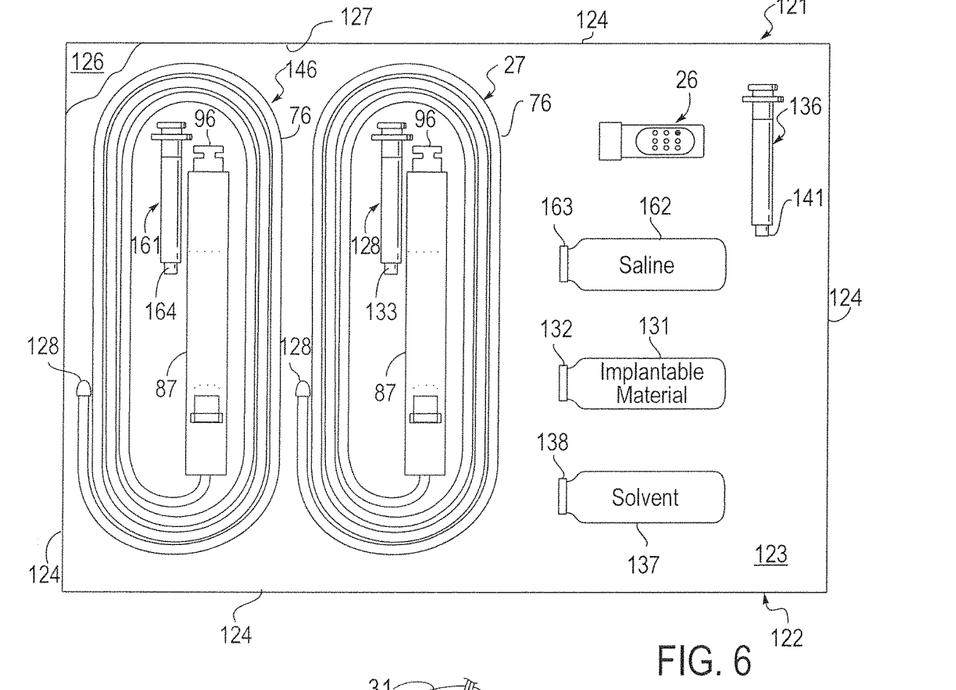
FIG. 6 is a plan view of a kit, somewhat schematic and partially cut away, that includes the injection device of FIG. 4 for treating tissue in a passageway of a mammalian body.

A kit 121 for a use in treating tissue in accordance with one embodiment of the method of the present invention, for example tissue in a wall forming the upper portion of a gastrointestinal tract in a human body, is shown schematically in FIG. 6. Kit 121 includes a package 122 made from any suitable material such as cardboard or plastic for carrying the contents thereof. An exemplary package 122, shown in FIG. 6, is a box formed from a bottom wall 123, four side walls 124 and a top wall 126. A portion of top wall 126 is cut away in FIG. 6 to reveal an internal space 127 formed by walls 123, 124 and 126. The contents of receptacle or package 122 are disposed in internal space 127.

Injection apparatus 27 is carried by package 122 within internal space 127. As discussed above, the injection apparatus 27 includes outer sheath 76 joined to housing 87. Injection apparatus 27 is preferably shipped with locking mechanism 104 engaged so that slide 101 is retained by latch 108 in its first position shown in FIG. 4 and thus needle 79 is recessed within distal extremity 76b of the outer sheath 76. A cap 128 is removably attached to distal extremity 76b of the outer sheath 76 for protecting users against undesirable punctures by needle 79 during storage and setup. Tissue capture member 26 is optionally carried within the internal space 127 of the package 122.

A reservoir or supply 28, for example in the form of a syringe 28, and a container or vial 131 of a suitable injectable material, for example of the type referred to above, is optionally included, separately or together, within kit 121. Where vial 131, shown with cap 132 in FIG. 5, contains a solution, for example of an implant-forming material disposed within a liquid, luer fitting portion 133 of the syringe 28 is removably coupleable to cap 132 of the vial 131. The luer fitting portion 133 of the syringe 28 is also removably coupleable to fitting 96 provided on housing 87 of injection apparatus 27. Additional optional components of kit 121 include a second reservoir or supply, such as syringe 136, and a container of a biocompatible solvent such as DMSO in the form of vial 137. Vial 137 includes a cap 138 and syringe 136 has a luer fitting portion 141 removably coupleable to cap 138 of the vial 137.

Kit 121 optionally further includes an additional or second needle assembly or injection device 146 which is of any suitable type and preferably substantially identical to injection apparatus 27. Accordingly, like reference numerals have been used in FIG. 6 to describe like components of injections apparatus 27 and 146. Further optional components of kit 121 include a third reservoir or supply, such as syringe 161, and a container or vial 162 of an aqueous solution such as a saline solution. Vial 162 includes a cap 163 and syringe 161 has a luer fitting portion 164 removably coupleable to cap 163 of the vial 161.

Figure 7:
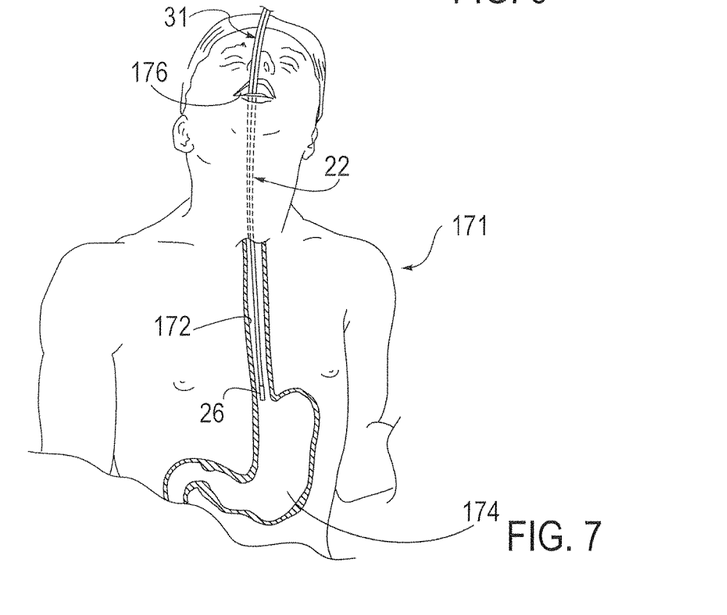
FIG. 7 is a schematic view of a portion of the apparatus for treating tissue of FIG. 1 practicing a method in accordance with one embodiment of the present invention in a passageway of a mammalian body.
Figure 8:
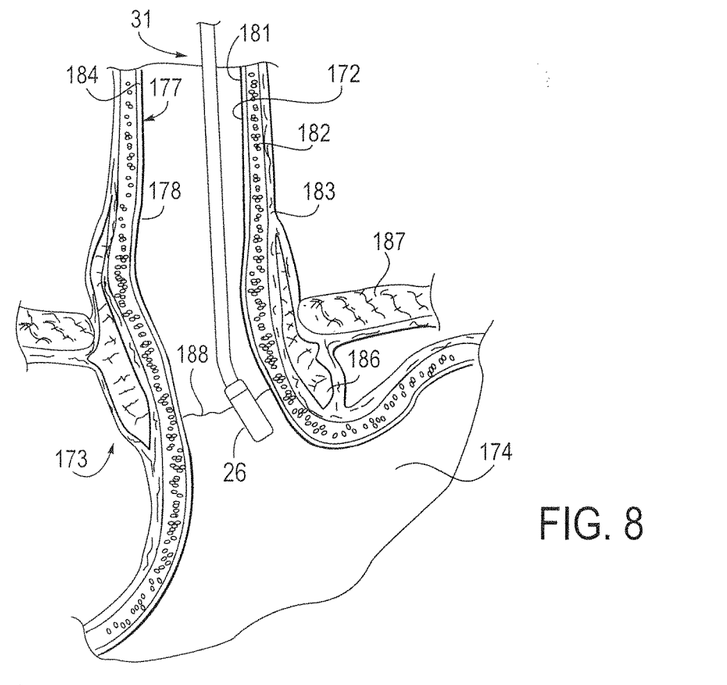
FIG. 8 is an enlarged view of a portion of the apparatus for treating tissue of FIG. 1 practicing the method of the present invention in the passageway of a mammalian body of FIG. 7.
Figure 9:
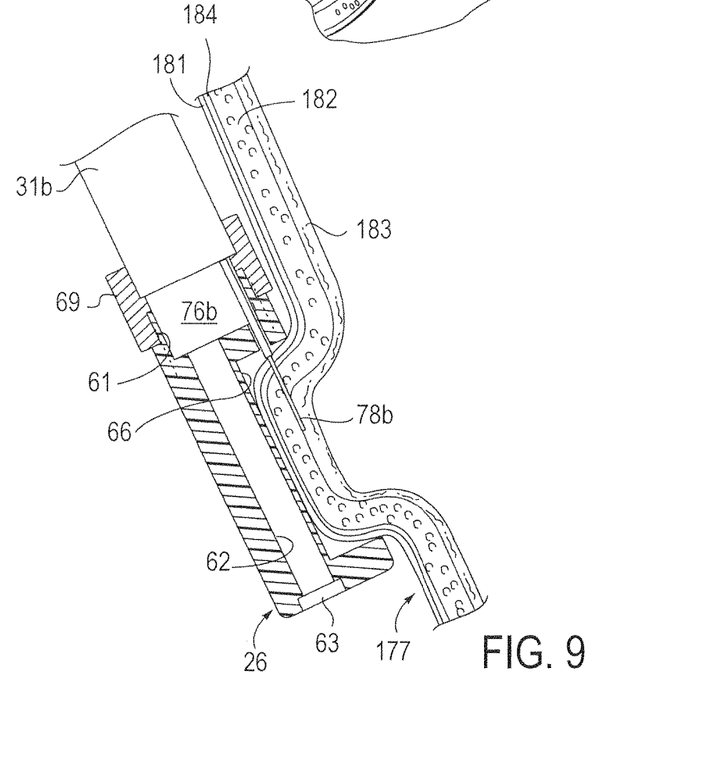
FIG. 9 is a side view, similar to FIG. 3, of the distal extremity of the apparatus for treating tissue of FIG. 1 receiving a portion of a wall forming a passageway of a mammalian body of FIG. 7.

To assist in describing the utilization of the apparatus and practice of one embodiment of the method of the present invention, a portion of a mammalian body, in this case a human body 171, is shown in FIGS. 7-9. Body 171 has an internal cavity in the form of the passage of the esophagus 172 extending through a lower esophageal sphincter 173 to a stomach 174. Such cavity is accessible by a natural body opening in the form of mouth 176 and is defined by a wall 177 having a surface 178 which surrounds the esophagus. Esophagus 172 is part of the gastrointestinal tract of body 171 that extends from mouth 176 to an anus (not shown). The esophageal mucosa 181 serves as the inner layer of the intraluminal wall 177 in the esophagus 172. Wall 177 has a plurality of tissue layers, including a muscle layer comprising layer of circular muscle 182 extending beneath mucosa layer 181 and layer of longitudinal muscle 183 beneath circular muscle 182. The muscle layers 182 and 183 each extend around the esophagus 172 and the stomach 174. Wall 177 further includes a submucosal layer or submucosa 184 extending between mucosa 181 and muscle layers 182 and 183. A submucosal space, that is a potential space, can be created between submucosa 184 and circular muscle layer 182 by the separation of layer 181 from muscle layer 182. In addition, as with any muscle, wall 177 includes an intramuscular potential space, that is a space which can be created intramuscularly by distension and separation of muscle fibers within a single muscle, such as for example separation or dissection of circular muscle layer 182 from longitudinal muscle layer 183. Wall 177 has a depth or thickness which includes at least mucosal layer 181, submucosal layer 184, circular muscle layer 182 and longitudinal muscle layer 183. The phreno-esophageal ligament 186 and diaphragm 187 extend around the esophagus 172 above the lower esophageal sphincter 173. "In the vicinity of the lower esophageal sphincter," as that term is used herein, includes at least the lower third of the esophagus 172, the squamous columnar junction 188, and the gastric cardia or upper portion of the stomach 174.

Although medical device 21 can be operated and used in any number of procedures, in one exemplary procedure the device is introduced into a natural body opening to access a vessel in the body such as a passageway or an organ. In a further exemplary procedure, device 21 can be utilized to deliver of a material, such as a fluid, solution or composition, to a wall of a passageway within a mammalian body to treat the body and more particularly to treat the wall forming the gastrointestinal tract of a mammalian body. Such exemplary procedures include the procedures described in part in U.S. Pat. Nos. 6,238,335, 6,251,063, 6,575,896, 6,358,197 and 6,695,764, the entire content of each of which is incorporated herein by this reference. The exemplary procedure utilized for describing the devices and methods of the present invention is the treatment of gastroesophageal reflux disease.

In one exemplary procedure of the present invention, a saline or other aqueous solution is introduced into wall 177 to separate tissue layers of the wall and thus create a pocket into which an injectable material is introduced. In this procedure, the saline is injected into the wall 177 by any suitable means such as through injection apparatus 27 or second injection apparatus 146.

Probe 22 is prepared by connecting cable 42 to light source 43 and attaching the proper eye piece 41 to probe handle 33. In addition, all other conventional attachments are applied to probe 22. Kit 121 is then opened and tissue capture member 26 mounted on distal extremity 31b of the insertion tube 31. In this regard, attachment outer sheath 69 is slid over the distal extremity of the insertion tube 31 until distal face 32 of the insertion tube abuts proximal end 57a of end cap 57. Suction source 72 is coupled to handle 33 in a conventional manner so as to permit the application of suction or negative pressure to apertures 68 provided in base 67 of suction chamber 66.

Second injection apparatus 146 is then removed from kit 121 and distal extremity 76b of the outer sheath 76 is inserted into side port 46 of probe 22 and slid through probe passageway 36 until outer sheath distal extremity 76b is in the vicinity of distal extremity of 31b of the insertion tube 31. Outer sheath distal extremity 76b preferably does not extend into suction chamber 66 of tissue capture member 26 and more preferably is recessed within distal extremity 31b of the insertion tube 31. Markings (not shown) can be provided on proximal extremity 76a of outer sheath 76 for positioning relative to side port 46 so as to monitor in a conventional manner the position of outer sheath distal extremity 76b with respect to insertion tube distal extremity 31b. A supply of saline or another aqueous solution is coupled to injection apparatus 146. For example, saline from vial 162 in kit 121 is loaded into syringe 161 and luer fitting portion 164 of the syringe 161 coupled to luer fitting 96 of the injection apparatus 146.

After the patient has been appropriately sedated or anesthetized, probe handle 33 is grasped by the physician to introduce distal extremity 31b of probe 22 into mouth 176 and advance insertion tube 31 down esophagus to the vicinity of the lower esophageal sphincter 173. Insertion tube 31 and outer sheath 76 each have a length so that when respective distal extremities 31b and 76b are in the vicinity of the tissue being treated, in this case in the vicinity of lower esophageal sphincter 173, respective proximal extremities 31a and 76a are outside of the body 171.

Under the guidance of optical viewing device 23, which can view distally of tissue capture member 26 by means of central bore 62 and optical window 63 and can further view through the tissue capture member 26 if end cap 57 is formed from an optically clear material, the physician moves distal extremity 31b of the insertion tube to the appropriate location near lower esophageal sphincter 173 (see FIG. 8). Thereafter, suction chamber 66 of the tissue capture member 26 is positioned adjacent to the portion of the esophageal wall 177 to be treated. Suction source 72 is actuated to draw air from and evacuate suction chamber 66 so as to create a negative pressure within the suction chamber and draw the targeted tissue, that is the portion of wall 177 to be treated, into suction chamber 66 (see FIG. 9).

The physician primes inner sheath 78 of second injection apparatus 146 with the saline or other aqueous or physiologic solution from syringe 161 and ensures that the passageway of the inner sheath 78 is filled with the solution by observing, with optical viewing device 23, solution being dispelled from the opening in needle 79.

Distal extremity 76b of outer sheath 76 is further advanced through passageway 36 of insertion tube 31 to a desired position for penetrating needle 79 into the targeted tissue within suction chamber 66. Preferably, outer sheath distal extremity 76b is advanced out from the passageway 36 to a position within tissue capture member 26. In one preferred method of the invention, outer sheath distal extremity 76b is advanced through access bore 71 until the outer sheath engages the tissue wall 177 within suction chamber 66. In other suitable procedures, outer sheath distal extremity 76b can be advanced to any predetermined position, for example at a desired position within access bore 71, which can be monitored by the position of outer sheath proximal extremity 76a relative to side port 46.

Slide 101 is released within internal chamber 88 to drive needle 79 distally from outer sheath lumen 77 to its second position and into the tissue wall 177 disposed within suction chamber 66 of tissue capture member 26. In this step, lever 111 is depressed by a finger such as the thumb of the operating physician to pivot locking element 106 about pin 107 and release latch 108 so as to permit the slide 101 to move distally or forwardly within chamber 88 under the force of coil spring 102. As discussed above, the components of spring mechanism 86 are appropriately sized to cause needle 79 to move distally a predetermined distance within suction chamber 66 and the tissue therein. The plunger of syringe 161 is thereafter depressed to urge saline from inner sheath 78 into wall 177 and form a pocket or void (not shown) therein. In this regard, and as shown in FIG. 9 where needle 79 is disposed between circular muscle layer 182 and longitudinal muscle layer 183, the saline serves to separate tissue layers of the wall 177 when forming such pocket or void. The amount of injected saline can be predetermined and monitored by the extent to which the plunger of syringe 161 is depressed. Second injection apparatus 146 is subsequently withdrawn from passageway 36 of insertion tube 31, causing needle 79 to withdraw from the tissue within suction chamber 66.

Injection apparatus 27 is now removed from kit 121 and prepared for use. An implantable or other injectable material from vial 131 is loaded into syringe 128 and luer fitting portion 133 of the syringe coupled to luer fitting 96 of injection apparatus 27. Outer sheath distal extremity 76b of the injection apparatus 27 is inserted through side port 46 into passageway 36 of insertion tube 31 and thereafter advanced in the manner discussed above with respect to injection apparatus 146 until the outer sheath distal extremity 76b is in the desired position, preferably within tissue capture member 26, for launching needle 79 of the apparatus 27 into the targeted tissue within suction chamber 66. Either before or after such insertion of outer sheath 76 into passageway 36, the inner sheath 78 can be primed with the implantable, implant-forming or other injectable material from syringe 128. As part of this step, a predetermined amount of such material is introduced into the inner sheath or a sufficient amount of material dispensed from syringe 128 until the material is available at the distal opening in needle 79. Where the inner sheath 78 is primed while disposed within insertion tube 31, it may be advantageous to observe the injectable material at the opening of needle 79 before outer sheath distal extremity 76b is moved to its final position for launching needle 79 if such position, for example as shown in FIG. 9, is not readily observable by optical viewing device 23.

Injection apparatus 27 is actuated in the same manner discussed above with respect to second injection apparatus 146 to introduce needle 79 into the tissue of wall 177. The distal opening of the needle is preferably disposed within the saline pocket formed by second injection apparatus 146. Where injection apparatus 27 and 146 are identical in configuration, as disclosed herein, and the distal ends of the respective outer sheaths 76 have been similarly positioned within medical device 21 for injection of the respective needles 79, the placement of the distal opening in needle 79 of injection apparatus 27 within the saline-filled void is likely. The plunger of syringe 128 is depressed to urge material from inner sheath 78 into the targeted tissue within wall 177. A predetermined amount of material can be so injected by monitoring the movement of the plunger relative to the barrel of syringe 128. The amount of material so injected can be greater than, less than or equal to the amount of saline previously injected into the tissue wall 177. In one preferable embodiment, the amount of injected material is approximately equal to the amount of injected saline.

An implant can be formed from implant-forming material injected within the saline void previously formed in the targeted tissue, in this instance for enhancing wall 177 for the treatment of gastroesophageal reflux disease. In an exemplary procedure, the implant is formed beneath submucosa 184 and thus in or along one or both of circular muscle layer 182 and longitudinal muscle 183 and thus serves to reduce the distensibility of wall 177 in the vicinity of lower esophageal sphincter 173.

One or more implants can be so formed within wall 177 in accordance with the foregoing procedure. Multiple implants can be formed by sequentially repeating such procedure or by creating a plurality of saline voids within wall 177 by use of second injection apparatus 146 and, thereafter, filing such voids with the implant-forming material by means of injection apparatus 127. Preferably a plurality of implants are formed in the tissue wall 177 and arranged in any suitable configuration, for example any of the configurations of implants disclosed in U.S. Pat. No. 6,251,063. Implants can be formed in any or all of the layers of wall 177, including between any of such layers. The one or more implants can be of any suitable shape, for example an arcuate implant which extends around a portion or all of the wall as disclosed in U.S. Pat. No. 6,251,064, the entire content of which is incorporated herein by this reference. The implants can serve to augment the wall, bulk the wall, reduce the distensibility of one or both of the muscle layers 182 and 183 of the wall or serve any other purpose for treating the wall.

Injection apparatus 27 and 146, and tissue capture member 26, facilitate the repeatable injection of material in the tissue of wall 177, for example the repeatable formation of implants in tissue wall 177 as well as the proper placement of such implants in the tissue wall. Each of the devices assists in placement of the implants at a predetermined and desired depth in the tissue wall and inhibit undesirable extension of the injection needle through the tissue wall into adjacent regions of the body. In this regard, tissue capture member 26 advantageously causes needle 79 to enter tissue wall 177 in a direction parallel to the longitudinal axis of the esophagus.

It is appreciated that a single injection apparatus 27 or 146 can be utilized for both introducing saline into tissue wall 177, for formation of a saline void or otherwise, and introducing the injectable material into the wall. Where a single injection apparatus is utilized to first inject saline and then inject another material, it may be preferable to cleanse the passage of inner sheath 78 of such injection apparatus with solvent, for example from vial 137 and by use of syringe 136, to ensure that the saline solution has been removed from the passageway of inner sheath 78 before the second material is injected through the inner sheath. Where the second material is an implant-forming material, the removal of the saline solution from the inner sheath 78 can inhibit premature precipitation or other formation of a solid from the implant-forming material where the formation of such solid is initialized or enhanced by the mixture of such material with a saline or other aqueous solution.

It is further appreciated that other injection apparatus, such as conventional injection apparatus, can be used for injecting one or both of the saline and the second material into tissue wall 177. Also, it is appreciated that the second material, for example an implant-forming material, can be injected into tissue wall 177 without the prior injection of a saline or aqueous solution, that is without the prior formation of a pocket of saline or other aqueous solution. In such a procedure, a single injection apparatus, such as injection apparatus 27, can be utilized.

Figure 10:
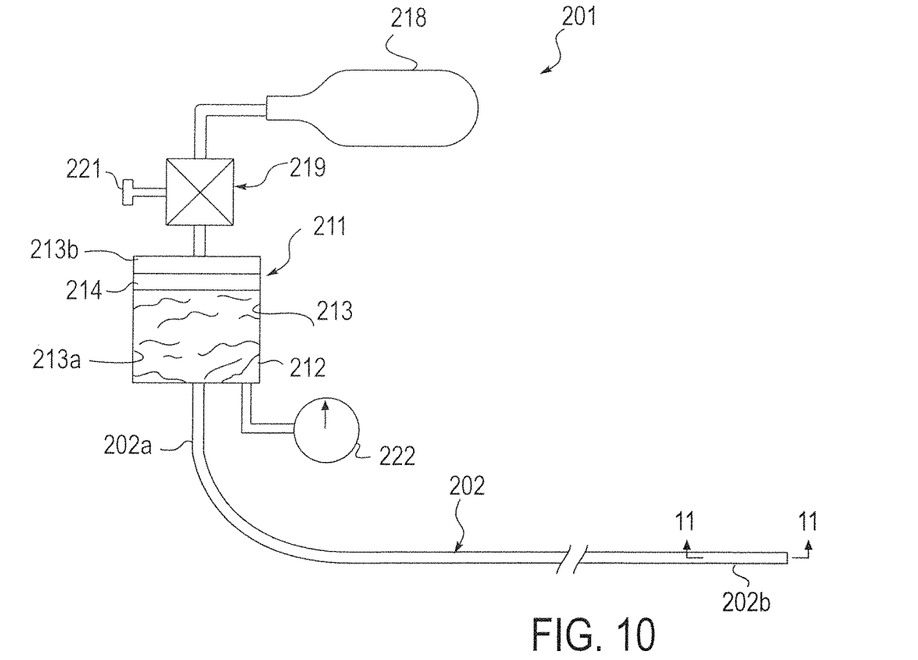
FIG. 10 is a side elevational view, partially cut away, of another embodiment of an injection device for use as part of the apparatus for treating tissue of the present invention.
Figure 11:
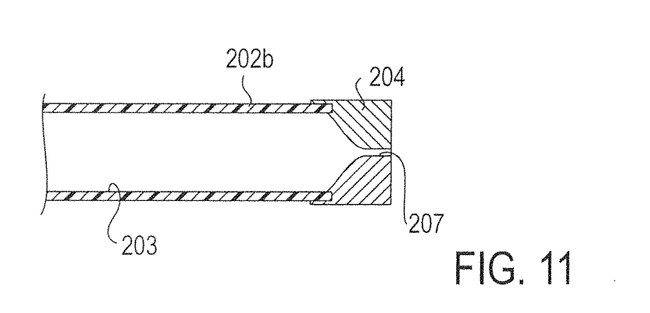
FIG. 11 is a cross-sectional view, taken along the line 11-11 of FIG. 10, of the distal extremity of the injection device of FIG. 10.
Figure 12:
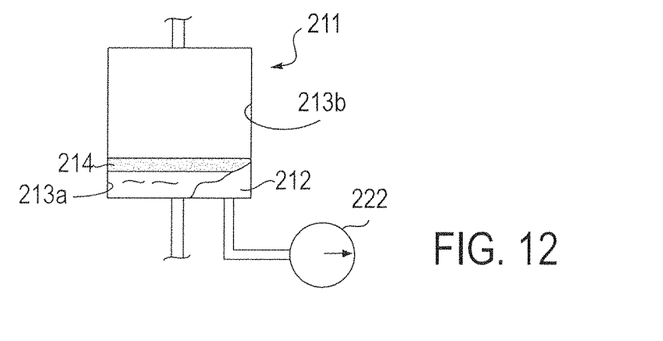
FIG. 12 is a side elevational view, partially cut away, of a portion of the injection device of FIG. 10 in a second position.

Other injection apparatus can be utilized with probe 22 and tissue capture member 26. Injection apparatus or injector 201 illustrated schematically in FIGS. 10-12 provides for a needleless injection of material into tissue of body 171. In this regard, injector 201 includes an elongate tubular member 202 having a diameter and length similar to outer sheath 76 so as to permit insertion of tubular member 202 into passageway 36 of probe 22. The tubular member 202 has a proximal extremity 202a and a distal extremity 202b and is made from any suitable material such as plastic. A lumen or passageway 203 extends from the proximal extremity 202a to the distal extremity 202b and a nozzle 204 is carried by the distal extremity 202b (see FIG. 11). Nozzle 204 is made from any suitable material such as stainless steel and is secured to distal extremity 202b of elongate tubular member 202 by a suitable means such as an adhesive. An outlet orifice 207 is provided in the nozzle and communicates with lumen 203 of the tubular member 202. The diameter of orifice 207 is smaller than the internal diameter of elongate tubular member 202 so as to provide for a significant increase in the velocity of the material when dispensed by nozzle 204. More specifically, lumen 203 of the tubular member 202 has an internal diameter ranging from 0.1 to 2.0 millimeters and preferably approximately one millimeter and orifice 207 has diameter ranging from 0.05 to 0.5 millimeter and preferably approximately 0.2 millimeter.

A supply 211 of an injectable material is coupled to proximal extremity 202a of the injector 201. In one embodiment, supply includes a fluid reservoir 212 provided with an internal cavity 213 for holding a fluid such as a solution of an implant-forming material of the type described above. The reservoir 212 is made from any suitable material such as plastic. A piston 214 made from plastic or another suitable material is slidably disposed within cavity 213 and is sized and configured to provide a fluid-tight seal with the peripheral wall of reservoir 212 so as to fluidly divide cavity 213 into an injectable material portion 213a and a drive fluid portion 213b. A pressurized fluid source such as a hydraulic pressure source 218 is coupled to reservoir 212 and, more specifically, drive fluid portion 213b of the reservoir. The liquid of source 218 can be of any suitable type and has a pressure ranging from 1000 to 50,000 psi, preferably from 10,000 to 25,000 psi and more preferably approximately 18,000 psi. A valve 219 is disposed between pressure source 218 and reservoir 212 for controlling the flow of liquid from source 218 into drive fluid portion 213b of the cavity 213 and. thus, controlling the pressure within the drive fluid portion 213b. Valve 219 includes a valve actuator 221 for restricting or controlling the flow of liquid through the valve. An optional fluid pressure gauge 222 is coupled to injectable material portion 213a of reservoir 212 for monitoring the pressure of the injectable material within cavity 213.

Hydraulic pressure source 218, valve 219 and pressure gauge 222 are detachable from injector 201 so as to permit use of such components with other similar injectors 201. Furthermore, a port (not shown) can be provided in reservoir 212 for loading a fluid or other material into injectable material portion 213a of the reservoir 213. One or more of injectors 201 can be included within kit 121 in place of one or both injection apparatus 27 and 146 shown in FIG. 6. Where two injectors 201 are included within the kit, an hydraulic pressure source 218, valve 219 and pressure gauge 222 can be provided for each injector 201 or a single set of such components can be provided for both injectors 201.

In operation and use, one or more injectors 201 can be used in a method for treating tissue, such as the method described above for treating gastroesophageal reflux disease. For example, an injector 201 can be loaded with a material from vial 131 for use in injecting such material into targeted tissue wall 177. An optional second injector 201 can be loaded with an aqueous solution such as saline from vial 162, or other material, for injecting such solution or material into the tissue wall 177, for example prior to the injection of the first material in the wall. For simplicity, use of injector 201 will be described in a procedure where an implant-forming material is injected into tissue wall 177 without a prior or subsequent injection of an aqueous solution.

After an injector 201 with an elongate tubular member 202 and a supply 211, a pressure source 218, a valve 219 and a pressure gauge 222 are removed from kit 121, the pressure gauge and valve are coupled to reservoir 212 and the pressure source 218 is coupled to valve 219. Thereafter, the implant-forming material from vial 131 is loaded into injectable material portion 213a of reservoir 212. Elongate tubular member 202 is inserted into side port 46 of probe 22 and advanced through passageway 36 until distal extremity 202b of the elongate tubular member is in the vicinity of distal extremity 31b of the insertion tube 31.

Insertion tube 31 is introduced into body 171 and the desired portion of wall tissue 177 captured within suction chamber 66 of tissue capture member 26, in the manner discussed above. Distal extremity 202b of injector 201 is desirably positioned within tissue capture member 26, for example adjacent tissue wall 177 in the same manner as shown in FIG. 9 with respect to outer sheath distal extremity 76b of injector apparatus 27.

Valve 219 is opened, for example by depression of valve actuator 221, so as to cause the pressurized liquid within source 218 to flow through the valve 219 and into the drive fluid portion 213h of reservoir cavity 213. Under the force of such pressurized liquid, piston 214 is movable from a first position, shown in FIG. 10 in which the implant-forming material is available at nozzle 204, to a second position shown in FIG. 12, in which the implant-forming material is driven at high velocity through orifice 207 and into tissue wall 177. As illustrated in FIG. 12, the pressure within injectable material portion of 213a of cavity 213 increases, as shown by the indicator on pressure gauge 222, when piston 214 moves to its second position. Nozzle orifice 207 is constructed and the pressure within source 218 is provided so that the implant-forming material is driven into tissue wall 177 to a desired depth. In this regard, the implant-forming material exits nozzle 204 with a velocity ranging from 20 to 150 meters per second and preferably approximately 80 meters per second. As discussed above with respect to injection apparatus 27, tissue capture member 26 can be repositioned within the esophagus 172 for providing any number of additional implants, if desired, in tissue wall 177.

Where two materials are to be injected into tissue wall 177, for example a first injection of an aqueous solution for creating a pocket or void and a second injection of an implant-forming material for creating an implant in such void, injector 201 can be used for one of such injections and any other suitable injection apparatus, for example injection apparatus 27, can be utilized for injecting the other material.

Figure 13:
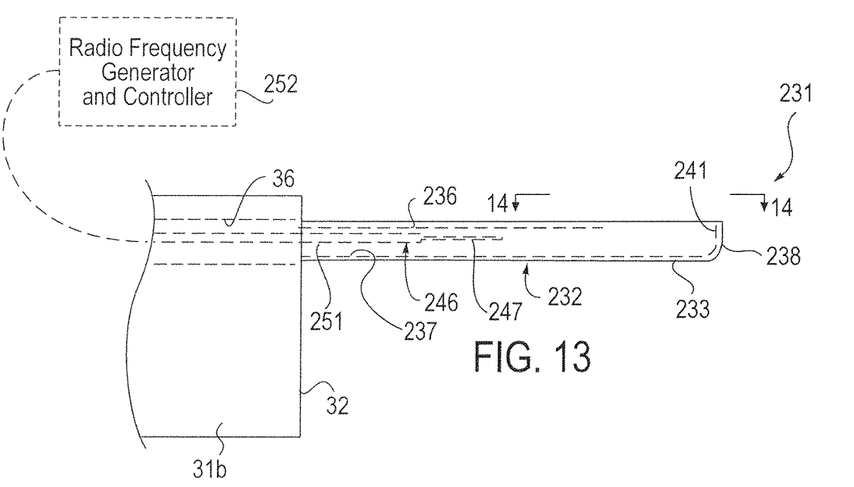
FIG. 13 is a side elevational view of another embodiment of an apparatus for treating tissue of the present invention.
Figure 14:
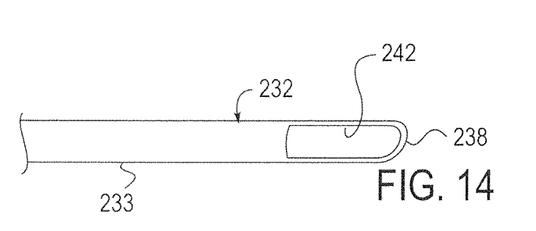
FIG. 14 is a top plan view, taken along the line 14-14 of FIG. 13, of a distal portion of the apparatus for treating tissue of FIG. 13.
Figure 15:
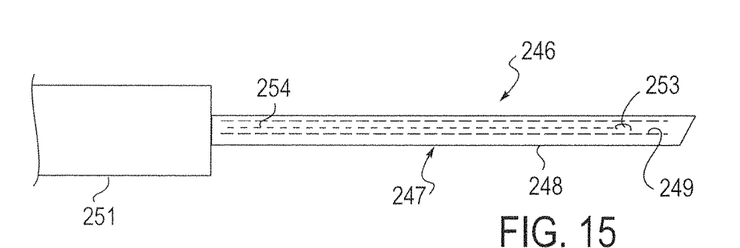
FIG. 15 is a side elevational view of a distal portion of a needle, shown in dashed lines in the apparatus for treating tissue of FIG. 13.

Other embodiments of apparatus for treating tissue can be provided. One such embodiment includes a treatment apparatus 231 for use with probe 22. The treatment apparatus 231, a portion of which is shown in FIGS. 13-15, includes an elongate tubular member or suction tube 232 sized for slidable disposition within passageway 36 of the probe 22. In this regard, suction tube 232 has an outer diameter ranging from 1.5 to 3.0 millimeters and preferably approximately 2.3 millimeters. The suction tube 232 is made from stainless steel or any other suitable material and has a proximal portion or extremity (not shown) and a distal portion or extremity 233. Elongate suction tube 232 is preferably cylindrical in conformation, being formed with an outer cylindrical wall 236 and an elongate passageway or lumen 237 formed by the wall 236 and extending from the proximal extremity to the distal extremity of the suction tube 232. Suction tube 232 is formed with a rounded distal end 238 and cylindrical wall 236 is provided with at least one opening 241 therein, preferably adjacent distal end 238, which communicates with lumen 237. The opening 241, together with the underlying portion of lumen 237, forms a recess or suction chamber 242 extending through cylindrical wall 236 and opening on to the outer surface of such wall and suction tube 232. Suction chamber 242 can be of any suitable size and configuration, preferably having a length ranging from one to five centimeters, more preferably approximately three centimeters, and extending circumferentially over an angle ranging from 30 to 180 degrees, more preferably approximately 90 degrees. A suitable suction source, such as suction source 72, can be coupled to the proximal extremity of an elongate suction tube 232 for providing a negative pressure within lumen 237 and thus suction chamber 242.

Distal extremity 233 of the elongate suction tube 232 is movable between a first position (not shown), in which suction chamber 242 is disposed within insertion tube 31, and a second position shown in FIG. 13, in which suction chamber 242 is accessible distally of insertion tube 31 and preferably fully exposed outside of the insertion tube.

A stylet 246 is slidably disposed within lumen 237 of elongate suction tube 232, and thus the stylet 246 is slidably disposed within passageway 36 of insertion tube 31. Stylet 246 has a diameter ranging from 0.25 to 1.00 millimeter and preferably approximately 0.50 millimeter. The stylet 246 includes a needle member 247 made from any suitable conductive material such as stainless steel and having a proximal end portion or extremity (not shown) and a distal end portion or extremity 248 with a tissue penetrating tip. Needle member 247 preferably includes an elongate lumen 249 extending from its proximal end portion to its distal end portion 248. Stylet 246 optionally has a layer of insulating material 251 extending around needle member 247 but exposing the distal end portion 248 of the needle member. Such layer of insulating material is preferably in the form of an insulating sleeve or outer sheath 251, which can be either fixed relative to needle member 247 or slidably disposed on the needle member. When the insulating sleeve 251 is slidably disposed on or longitudinally movable with respect to needle member 247, the needle member is movable between a first position (not shown) in which its distal end portion 248 is recessed within insulating sleeve 251 and a second position in which end portion 248 extends distally of the sleeve 251, as shown in FIGS. 13 and 15.

A radio frequency generator and controller 252, shown schematically in phantom lines in FIG. 13, is electrically coupled to the proximal end portion of needle member 247 for supplying radio frequency energy to the needle member.

An optional temperature sensor 253 can be mounted to the distal end portion 248 of the needle member 247, for example in lumen 249 of the needle member 247. Sensor 253 is preferably disposed on distal end portion 248 of the needle member and is electrically coupled by a suitable lead 254 to radio frequency generator and controller 252 for providing temperature feedback regarding the needle member and thus surrounding targeted tissue to the controller. The radio frequency generator and controller 252 preferably includes temperature monitoring circuits.

Stylet 246, and needle member 247 thereof, are slidably or longitudinally moveable within lumen 237 of elongate suction tube 232 between a first position in which the tissue-penetrating tip of the needle member 247 is not disposed within suction chamber 242 and a second position in which the tissue penetrating tip is disposed in the suction chamber 242.

Treatment apparatus 231 can be used in any suitable procedure, such as the procedure described above for treating gastroesophageal reflux disease. In such a procedure, distal extremity 31b of insertion tube 31 is introduced into the esophagus 132 in the manner described above. Either before or after such insertion, distal extremity 233 of elongate suction tube 232 is introduced through side port 46 into passageway 36 of the insertion tube 31 and slid distally until distal extremity 233 is in the vicinity of distal extremity 31b of the insertion tube and preferably recessed within passageway 36. Under the guidance of optical viewing device 23, tube distal extremity 31b is brought to a position adjacent the tissue to be treated. The elongate suction tube 232 has a length such that when distal extremity 233 is in the vicinity of the tissue to be treated, for example the gastroesophageal sphincter, the proximal extremity of the suction tube 232 is outside of the body 171.

Elongate suction tube 232 is moved distally within passageway 36 from its first position in which suction chamber 242 is disposed within the passageway 236 to a second position, shown in FIG. 13, in which the suction chamber is outside of insertion tube 31. Suction chamber 242 is then maneuvered to a position adjacent tissue to be treated and suction from source 72 is provided to lumen 237 to urge or draw the desired portion of tissue wall 177 into suction chamber 242.

Treatment apparatus 231 can be utilized as a monopolar or bipolar device for ablating tissue wall 177. If a monopolar procedure is desired, an indifferent or ground electrode (not shown) can be affixed to the backside of the body 171 and electrically coupled to radio frequency and controller 252. If a bipolar operation is desired, the elongate suction tube 232 can be electrically coupled to radio frequency generator and controller 252 for serving as the ground electrode.

The tissue penetrating tip of needle member 247 is moved from its first position not disposed within suction chamber 242 to its second position disposed within suction chamber 242 so as to penetrate the tissue of wall 177 located within the suction chamber 242. Suction chamber 242 and needle member 247 are appropriately sized so that the exposed portion of needle member 242 extends into the desired layer of wall 177, for example one or both of muscle layers 182 and 183 or the submucosa or deep mucosa 184. The needle member 247 is then electrified to treat the targeted tissue. Preferably, radio frequency energy from generator and controller 252 is supplied to needle member 247 to ablate the tissue within suction chamber 242 and thus change the compliance of the targeted tissue. The suction chamber 242 is sufficiently deep so as to permit the ablation of relatively deep layers of wall 177, such as the circular and longitudinal muscle layers 182 and 183. In one preferred procedure, approximately 30 watts of energy is supplied to the needle member 247 for approximately ten seconds for creating a lesion in wall 177 ranging from 0.5 to three millimeters and preferably approximately two millimeters. The temperature of the tissue within suction chamber 242 is monitored by sensor 253. Feedback information from sensor 253 can be processed by generator and controller 252 to adjust the amount and duration of energy delivered to needle member 247. Conventional impedance feedback can also be utilized for controlling the delivery of energy through needle member 247. In this manner charring of the tissue and sticking between the needle member 247 and the tissue is inhibited. Multiple lesions can be formed, at one or more locations in tissue wall 177, in a single procedure.

In the same manner as discussed above with respect to tissue capture member 26, elongate suction tube 232 of apparatus 231 serves to provide for proper and repeatable lesion formation in tissue wall 177. In addition, undesirable extension of the inner sheath 78 fully through the tissue wall 177 is inhibited.

Stylet 246 of treatment apparatus 231 can be utilized without elongate suction tube 232 and be within the scope of the present invention. In one such procedure, stylet 246 is utilized with probe 22 having tissue capture member 26 mounted on distal extremity 31b thereof in the manner described above. Stylet 246 is introduced directly into passageway 36 of the insertion tube 31 by means of side port 46, and is movable between a first position in which distal end portion 248 of the needle member 247 is disposed within passageway 36 and a second position in which the distal end portion 248 extends distally of the insertion tube 31. Once tissue from wall 177 has been captured within suction chamber 66 of the tissue capture member 26 in the manner disclosed above, distal end portion 248 of needle member 247 is advanced from its first position, and through access bore 71 of tissue capture member 26, to a second position into the tissue within suction chamber 66. Radio frequency from radio frequency generator and controller 252 is supplied to needle member 247 for ablating the tissue within suction chamber 66. In a monopolar procedure, a return or an indifferent electrode is mounted to body 171, for example on the backside of the body, and coupled to radio frequency generator and controller 252 for serving as a return electrode.

Although stylet 246 has been disclosed for use with radio frequency energy, it is appreciated that stylet 246 can be configured to deliver other forms of electromagnetic energy, for example microwave or other electrical energy or light.

In a further embodiment of the invention, elongate suction tube 232 can be utilized with an injection needle of any suitable type in place of ablation needle member 247 so as to introduce an injectable material into the tissue captured within suction chamber 242 of the elongate suction tube 232. In this regard, a tubular needle, such as inner sheath 78, is slidably disposed within lumen 237 of suction tube 232 for movement between a first position in which the distal end portion of the needle is not disposed within suction chamber 242 and a second position in which the needle distal end portion is disposed within suction chamber 242. A suitable supply of an injectable material, such as supply 28, is fluidly coupled to the proximal end portion of such needle for supplying an implantable or other injectable material to the tissue within suction chamber 242. In alternative embodiments, each of injection apparatus 27 and 201 be scaled down for use with elongate suction tube.

It is appreciated that the apparatus and methods of the invention can be used with other devices to strengthen the structure of a readjusted lower esophageal sphincter. For example, the apparatus and methods disclosed above can be applied subsequent to a surgical fundoplication operation for the treatment of gastroesophageal reflux disease.

Although the apparatus and methods here have been disclosed for treating tissue in the upper portion of the gastrointestinal tract of a mammalian body, such apparatus and methods can be modified for use elsewhere in the gastrointestinal tract, such as in the vicinity of the anus or other lower portions of the gastrointestinal tract. In addition, the apparatus and methods disclosed herein can be utilized in other passageways and vessels of a body, as well as other areas of a body.

As can be seen from the foregoing, a method and apparatus have been provided for the repeatable treatment of tissue in a mammalian body. The treatment can include the formation of implants in the tissue wall or the injection of other material into the tissue wall, as well the creation of ablated tissue in the wall. In one embodiment of the present invention, improper placement of the implants or other injectable material and improper location of the ablated tissue is minimized.

What is claimed is:

1. A method for treating mammalian esophageal tissue with a flexible elongate member having a distal extremity provided with a recess, comprising:
    introducing the distal extremity into the body adjacent the esophageal tissue through an insertion tube;
    capturing the esophageal tissue in the recess;
    advancing a needle from a first position within the distal extremity to a second position within the recess and into the esophageal tissue captured in the recess, wherein the recess is capable of relative movement between a first position in which the recess is disposed within the insertion tube and a second position in which the recess is accessible distally of the insertion tube; and
    injecting a material through the needle into the esophageal tissue in the recess, wherein a travel distance of the needle between the first and second positions ranges from 4 to 25 millimeters.

2. The method of claim 1, wherein the needle is introduced into the recess by means of the flexible elongate member.

3. The method of claim 1, wherein the injected material comprises an antibiotic.

4. The method of claim 1, wherein the injected material comprises an analgesic.

5. The method of claim 1, wherein the injected material comprises an implant-forming material.

6. The method of claim 5, wherein the implant-forming material includes a nonbiodegradable solid.

7. The method of claim 1, wherein the injected material comprises a biocompatible polymer.

8. The method of claim 1, wherein the injected material comprises saline.

9. The method of claim 8, wherein the injected saline forms a pocket within the tissue.

10. A method for treating mammalian esophageal tissue with a flexible elongate member having a distal extremity provided with a recess, comprising:
    introducing the distal extremity into the body adjacent the esophageal tissue through an insertion tube;
    drawing the esophageal tissue in the recess using suction;
    advancing a needle from a first position within the distal extremity to a second position within the recess and into the esophageal tissue captured in the recess, wherein the recess is capable of relative movement between a first position in which the recess is disposed within the insertion tube and a second position in which the recess is accessible distally of the insertion tube; and
    injecting a material through the needle into the esophageal tissue in the recess, wherein a travel distance of the needle between the first and second positions ranges from 4 to 25 millimeters.

11. A method for treating mammalian esophageal tissue with a flexible elongate member having a distal extremity provided with a nozzle, comprising:
    introducing the distal extremity into the body adjacent the esophageal tissue through an insertion tube;
    capturing the esophageal tissue in a recess within the nozzle; and
    injecting a material through an outlet orifice of the nozzle into the esophageal tissue in the recess, wherein a diameter of the outlet orifice is less than an inner diameter of the flexible elongate member, wherein the recess is capable of relative movement between a first position in which the nozzle is disposed within the insertion tube and a second position in which the recess is accessible distally of the insertion tube.

12. The method of claim 10, wherein the needle is introduced into the recess by means of the flexible elongate member.

13. The method of claim 10, wherein the injected material comprises an antibiotic.

14. The method of claim 10, wherein the injected material comprises an analgesic.

15. The method of claim 10, wherein the injected material comprises an implant-forming material.

16. The method of claim 10, wherein the implant-forming material includes a nonbiodegradable solid.

17. The method of claim 11, wherein the needle is introduced into the recess by means of the flexible elongate member.

18. The method of claim 11, wherein the injected material comprises a biocompatible polymer.

19. The method of claim 11, wherein the injected material comprises saline.

20. The method of claim 19, wherein the injected saline forms a pocket within the tissue.

* * * * *